(12) United States Patent
Katz

(10) Patent No.: US 8,858,228 B2
(45) Date of Patent: *Oct. 14, 2014

(54) METHOD AND KIT FOR DENTAL IMPLANT DRILLING GUIDES

(76) Inventor: Howard Ian Katz, La Jolla, CA (US)

(*) Notice: Subject to any disclaimer, the term of this patent is extended or adjusted under 35 U.S.C. 154(b) by 58 days.

This patent is subject to a terminal disclaimer.

(21) Appl. No.: 13/420,536

(22) Filed: Mar. 14, 2012

(65) Prior Publication Data

US 2012/0251974 A1 Oct. 4, 2012

Related U.S. Application Data

(63) Continuation-in-part of application No. 13/183,386, filed on Jul. 14, 2011, now Pat. No. 8,535,055.

(60) Provisional application No. 61/468,259, filed on Mar. 28, 2011, provisional application No. 61/507,945, filed on Jul. 14, 2011.

(51) Int. Cl.

| | | |
|---|---|---|
| *A61C 3/04* | (2006.01) | |
| *A61C 19/04* | (2006.01) | |
| *A61C 13/36* | (2006.01) | |
| *A61C 1/08* | (2006.01) | |
| *A61C 8/00* | (2006.01) | |

(52) U.S. Cl.
CPC ............... *A61C 1/084* (2013.01); *A61C 8/0089* (2013.01); *A61C 8/0001* (2013.01)
USPC ............................. 433/75; 433/196; 433/215

(58) Field of Classification Search
USPC ............... 433/75, 76, 165, 172–176, 196, 72, 433/215; 606/96–98; 408/202, 241; 33/513–514
See application file for complete search history.

(56) References Cited

U.S. PATENT DOCUMENTS

| | | | | |
|---|---|---|---|---|
| 5,486,109 | A | * | 1/1996 | Hunter et al. .................... 433/72 |
| 5,538,424 | A | * | 7/1996 | Gelb ................................ 433/72 |
| 5,556,278 | A | * | 9/1996 | Meitner .......................... 433/75 |
| 5,743,916 | A | * | 4/1998 | Greenberg et al. ............ 606/102 |
| 5,876,204 | A | * | 3/1999 | Day et al. ....................... 433/173 |
| 5,989,025 | A | * | 11/1999 | Conley ............................ 433/76 |
| 6,099,313 | A | * | 8/2000 | Dorken et al. ................. 433/175 |
| 2006/0257817 | A1 | * | 11/2006 | Shelton .......................... 433/75 |
| 2008/0064005 | A1 | * | 3/2008 | Meitner .......................... 433/74 |
| 2008/0176187 | A1 | * | 7/2008 | Stumpel ........................ 433/196 |
| 2011/0111362 | A1 | * | 5/2011 | Haber ............................. 433/72 |

* cited by examiner

*Primary Examiner* — Todd Manahan
*Assistant Examiner* — Michael R Ballinger
(74) *Attorney, Agent, or Firm* — Stephen E. Zweig

(57) ABSTRACT

Method and kit for producing implant drilling guides positioned at the proper orientation to avoid inadvertent damage to critical regions of the patient's jaw when drilling to place dental implant screws. The method works by placing a small post device with x-ray visible depth markers in the root socket of the patient's tooth immediately after tooth extraction. The post device may additionally be configured to guide the drill at a position and angle that is different from that of the original tooth socket. This post device is used to construct a removable guide that anchors to the patient's adjacent teeth, and preserves the location and orientation of the extracted tooth root. Once the root socket is filled in with new bone, the guide, in conjunction with the X-ray post depth information, can be used to direct drilling along the same route as the old tooth root, thus avoiding critical structures.

10 Claims, 10 Drawing Sheets

METHOD AND KIT FOR DENTAL IMPLANT DRILLING GUIDES

CROSS REFERENCE TO RELATED APPLICATIONS

This application is a continuation in part of patent application Ser. No. 13/183,386, METHOD AND KIT FOR PRODUCING DENTAL IMPLANT DRILLING GUIDES", filed Jul. 14, 2011, inventor Howard Ian Katz, now U.S. Pat. No. 8,535,055 issued Sep. 17, 2013; both 13/183,386 and this application claim the priority benefit of provisional patent application 61/468,259, "Device that records the exact spatial position, location in the jawbone, root socket depth and orientation of a recently extracted tooth that may be used to locate an ideal site to replace a tooth. It measures the location and dimensions of a tooth socket seconds after a tooth has been extracted before the socket has began to heal", inventor Howard Ian Katz, filed Mar. 28, 2011; both 13/183,386 and this application also claim the priority benefit of provisional patent application 61/507,945, "METHOD AND KIT FOR PRODUCING DENTAL IMPLANT DRILLING GUIDES", inventor Howard Ian Katz, filed Jul. 14, 2011.

BACKGROUND OF THE INVENTION

1. Field of the Invention

This invention is in the field of dental implants and methods and kits to assist the dental implant process.

2. Description of the Related Art

Dental implants have become popular in recent years as a way to provide permanent artificial teeth to patients who have lost their original teeth and teeth roots. The basic concept is fairly simple. The dentist drills into the patient's jaw bone and implants an artificial tooth root, often made of titanium or other strong biocompatible material, which essentially resembles a small threaded screw. Natural bone, by a process called osseointegration, then fuses with this screw like artificial root. An artificial crown can then in turn be screwed into the artificial root, and to all intents and purposes, the dental implant then performs like a natural tooth.

If an adequate amount of natural bone remains after the extraction of the natural tooth root, then the implant process can commence soon after tooth extraction. However if, as is often the case, an inadequate amount of natural bone remains in the tooth socket after extraction of the natural root, the empty tooth socket may have to be first filled with artificial bone material. Over the course of a few months, the artificial bone filled empty socket will gradually fill in with new natural bone. The implant can then be drilled into this new natural bone.

In practice, installing implants is both complex and risky because there is little tolerance for error in the drilling step. The various bones of the jaw are often both very thin, and placed against other important structures. For example the bones of the upper jaw border on the delicate open sinus structures, and accidentally drilling into the sinus region is of course very bad. The bones of the lower jaw are also tricky to work with. In addition to the risk of the drill bit accidently extending outside the lower jaw bone, there are also various lower jaw structures, such nerve canals, blood vessels, and the like, where accidental drilling can cause substantial permanent damage to the patient.

As a result, general dentists who may be otherwise comfortable with other parts of the implant process, such as tooth extraction, filling up tooth sockets with artificial bone, and installing artificial crowns into previously installed implant roots, are often reluctant to do implant drilling. Instead, after tooth extraction, they will either fail to recommend an implant at all (and instead recommend a dental bridge), or alternatively send the patient to a specialist such as an oral surgeon or periodontist who will in turn do the drilling and implant.

Unfortunately, the general dentist is in a difficult conflict of interest situation here. This is because as a result of the implant referral, the general dentist will lose out on the subsequent implant revenue from that patient. Thus at present, implants, although they may give superior results, tend to be a bit underused.

Even oral surgeons and periodontists need specialized help to safely guide drilling, however. Here, to guide drilling, the present practice is to use computerized tomography and 3D materials fabrication technology (e.g. computer controlled steriolithography, CNC machining, and the like) to create a custom implant drilling guide. To do this, 3D image information on the structure of the patient's jaw, is used to determine the optimum drilling angle, and the computer controlled fabrication technology is then use to create a custom drilling guide. Such computerized tomography devices and 3D fabrication methods are very expensive, and as a result, implant guides alone can often cost around $1000 or more.

As another alternative, the dentist, oral surgeon, or periodontist can attempt to drill guided only by professional judgment and standard dental X-rays, and assume the risk of problems and complications that may result. However this is not a risk that most general dentists, or their insurance providers, usually wish to assume.

Alternative approaches include Tang, U.S. Pat. No. 7,097,451, who teaches a thermoplastic surgical template and method for performing dental implant osteotomies. Unfortunately Tang fails to suggest how such a template may be oriented properly with respect to critical structures in the patient's jaw.

As a result, there is a strong disconnect between the process of tooth extraction and the beginning of the implant process. Implants cross the discipline barriers between general dentistry and oral surgery/periodontry. This disconnect adds a substantial amount of expense to the dental implant process, and often results in patients being encouraged to adopt less optimal solutions, such as dental bridges.

BRIEF SUMMARY OF THE INVENTION

The present invention is based, in part, on the insight that the patient's natural tooth socket, and in particular the hole in the bone (root socket, extraction socket) left over when the patient's natural tooth root has been extracted, either itself a good location to subsequently locate an implant screw (at least once this natural root socket has filled in with new bone) or is at least an excellent reference point by which to locate the subsequent implant screw. This is because natural tooth root, originally avoided any critical structures such as nerves, and was usually well positioned with respect to the other surrounding bone. To the extent that the natural tooth root location is less than optimal, often an excellent implant screw location can be found by a simple angle or distance offset from the original natural tooth socket.

The present invention is also based, in part, on the insight that present practice, which typically determines the optimum angle for implant screw insertion days, weeks, or months after the natural tooth has been extracted, is suboptimum. Rather, the optimum time to determine the angle, depth, and location of the natural root socket is immediately after the natural tooth has been extracted.

In one embodiment, the invention is a method and kit for determining the angle, depth, and location of the natural root socket immediately after (or at least relatively soon after) extraction of the natural tooth. Once this angle, depth, and location information has been determined, the invention further provides a means to quickly produce an implant drilling guide or position fixation device that captures this information, and makes it available to guide subsequent implant drilling up to months and even years later. Thus once the original tooth socket has filled in with new bone, the record of the position and depth of the original tooth socket is well suited for providing a convenient reference for the subsequent implant drilling procedure The invention's method and kit is designed to function using equipment typically available in general dentistry offices, such as standard X-ray equipment, and the like, and does not require use of sophisticated and expensive computerized tomography and computer controlled plastics fabrication equipment. The invention's method and kit is also designed to be simple enough to be operated by general dentists, although of course it may also be used by oral surgeons, peridontists, and other specialists as well.

Thus in one embodiment, the invention may be a method and kit for drilling a dental implant socket for a dental implant screw in the mouth of a patient. This method will generally comprise extracting a tooth from patient's lower or upper jaw, thereby forming an extraction socket with at least one tooth root socket. This tooth root socket will correspond to the position of at least one root of the extracted tooth. Then, while the extraction socket remains open and unhealed, the practitioner will place a specially designed post device into the appropriate tooth root socket. The invention's post device is configured to determine the depth and angle of the tooth root socket (relative to the patient's jaw and teeth). This post device will often also be configured to help generate a template for guiding a drill bit for drilling a dental implant socket at an optimal angle and depth for a dental implant screw.

Note, however, that the optimal angle and depth for the dental implant screw need not always be the same angle and depth of the tooth root socket. Parent Ser. No. 13/183,386, the contents of which are incorporated herein by reference, taught that for such situations, guide blocks with secondary holes could be fabricated, where one hole would fit over the post device, and the other hole would serve, in conjunction with a guide, to guide the drill bit at a different offset or angle. By contrast, the present invention teaches an alternative approach, in which instead a plurality of different post devices may be devised with built-in different angle and orientation offsets for this purpose. The method will then use a position fixation device or guide to preserve the position and orientation of this post device relative to the patient's jaw and teeth. After this is done, the post device may be removed from the patient's mouth. The position fixation device may then be subsequently used by a practitioner to guide a drill bit to the optimal angle and depth to drill a socket in the jaw for a dental implant screw.

Thus in addition to the pole-like post devices previously taught in parent application Ser. No. 13/183,386, other types of post devices may be also provided in the invention's kit and used according to the invention's method.

In some embodiments, the post device, or family of post devices, may comprise a bottom probe portion and a top drilling orientation portion. Here, as previously taught in Ser. No. 13/183,368, the bottom probe portion may comprise an elongated probe with a probe axis. This bottom probe will generally have at least one radius small enough to penetrate substantially to the bottom of the tooth root socket.

However in contrast to the pole-like top portions previously taught in Ser. No. 13/183,386, in the present invention, the top portion (top drilling orientation portion) of the post device may comprise a larger radius or diameter portion with its own unique drilling axis. This drilling axis need not be collinear or even parallel with the probe axis on the bottom of the post device (which lines up according to the tooth root socket). Rather, depending upon the particular post device in question, the drilling axis may be offset from the probe axis and/or additionally may be set at a different angle from the probe axis. This top drilling orientation portion is generally configured to protrude outside of the tooth root socket, so that the various position fixation devices can use and preserve the direction and orientation of the top drilling orientation portion of the post device for subsequent use in drilling sockets for the various dental implant screws.

As will be discussed, a family of such post devices may be produced and sold in kit form, along with ancillary equipment. Here this family of post devices may, for example, be configured for at least some of the various positions that different human teeth occupy in human jaws, wherein for the individual post device in the plurality of post devices, the extent to which the drilling axis is offset from with the probe axis and the extent to which the drilling axis is not at the same angle as the probe axis, may be pre-determined based on either considerations of typical human jaw and tooth anatomy, considerations of atypical human jaw and tooth anatomy, or considerations of the patient's individual jaw and tooth anatomy.

As previously discussed in parent application Ser. No. 13/183,386, often the post device may have x-ray visible depth markers, at least on the probe portion, so that the depth of the post device may be X-ray visualized in the root of the patient's tooth immediately after tooth extraction. This post device, along with guideblocks, optional washers, reduction or expansion guides, and optional rapidly hardening position fixation devices or guide materials (such as acrylics or thermosetting materials) may be used to construct a removable position fixation device or guide that anchors to the patient's adjacent teeth, and preserves the location and orientation of the extracted tooth root. Often the tooth root and socket is then filled in with new bone and allowed to heal.

When the practitioner then desires to drill the dental implant socket, the guide, often in conjunction with the X-ray post depth information, can be used to direct drilling along the same route as the old tooth root, thus avoiding critical structures.

Alternatively, in some situations, the position fixation device or guide may be used to direct drilling to certain regions of the jaw bone, such as the interradicular bone, where implants may be safely implanted before the roots of the extracted tooth are filled in with new bone.

DETAILED DESCRIPTION OF THE INVENTION

Figures 1A, 1B, 1C, 1D, 1E, 1F, 1G, 1H:
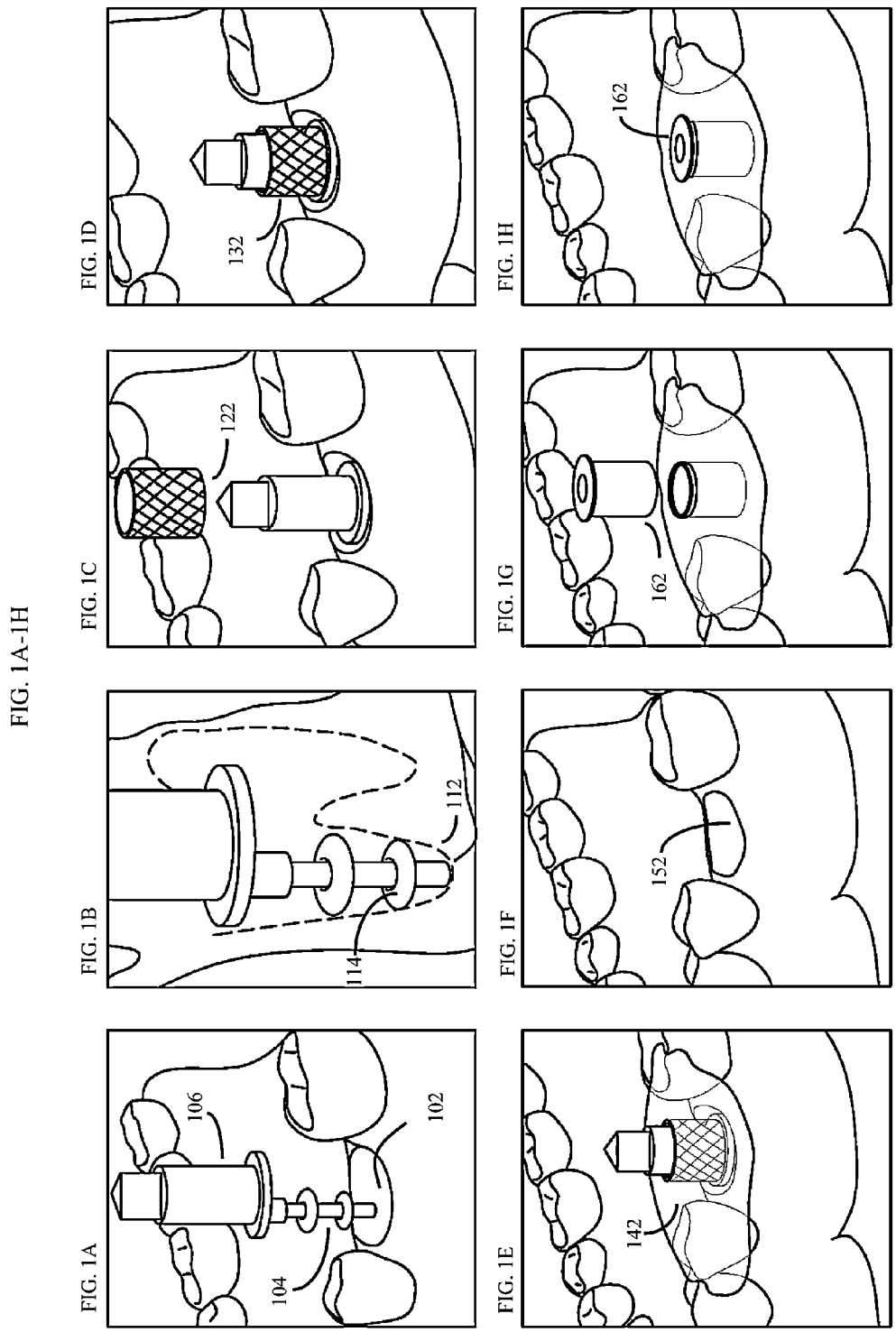
FIG. 1A-1H show the method in operation on a lower first molar tooth socket, using an offset post device where the direction of the drilling axis, formed by the top drilling orientation portion of the post device is offset, relative to the probe axis (of the bottom probe portion), in a lingual direction so that the drill can drill into the anatomically safe region formed by the jaw bone between the two molar tooth root sockets.

In one embodiment, the invention may be a method of aligning a dental implant based upon the position and depth of the natural tooth socket at the time of tooth extraction. The invention may also be a kit of components to accomplish this method. The method will generally comprise or at least start by extracting a tooth from the jaw of a human patient. This patient will generally have a fair number of other teeth, usually including other teeth reasonably adjacent to the empty tooth socket left in the patient's jaw, after the tooth has been extracted.

After this extraction, there will typically remain an extraction socket in the patient's jaw bone, and this extraction socket will in turn typically contain at least one tooth root socket in the jaw bone corresponding to the position of at least one root of the extracted tooth.

According to the method, while the extraction socket remains open and unhealed, a post device is placed into this at least one tooth root socket. This post device is generally configured to determine the depth and angle of this tooth root socket relative to the patient's jaw bone (e.g. relative to the position of nearby remaining teeth adjacent to the extraction socket and tooth root socket, which in turn are anchored firmly to the patient's jaw bone).

The post device used for this method is typically configured to also serve as a template for guiding a drill bit for drilling a dental implant socket at an optimal angle and depth for a dental implant screw for that particular tooth socket. Here the optimal angle and depth will generally be one that will both avoid vital structures (i.e. nerves, sinus cavities, blood vessels) and which will also remain inside the bone (i.e. not accidentally penetrate outside the jaw bone). The dental implant socket should also serve as a good foundation for the dental implant screw that will be later placed in the dental implant socket. Thus the surrounding bone should ideally not be too thin.

Note that due to the different anatomy of the various teeth relative to various other vital structures in the head, as well as individual differences between patients, the optimal angle and depth for the dental implant screw need not be exactly the same as the angle and depth of the original tooth root socket. That is, although tooth root socket locations are often excellent choices (generally after they have been filled in with bone or artificial bone), for drilling subsequent dental implant sockets, this is not always the case. Often other anatomical considerations require that the dental implant socket be displaced from the location or the angle of the original tooth root socket by some precise and defined amount.

After the post device has been placed in the appropriate open tooth root socket, the position and orientation of this post device, relative to the patient's jaw bone and adjacent teeth, can then be preserved by a position fixation device or guide device. Once the appropriate position fixation device or guide device has been adjusted, the post device can then be removed from the patient's mouth. The position fixation device will also usually be removed from the patient's mouth as well, and then preserved for later use.

Generally (but not always) after the empty tooth socket and empty tooth root socket has been filled in with bone or artificial material and allowed to heal, the position fixation device may then be reapplied to the patient's mouth, and this position fixation device can then be used to guide a drill bit (for drilling the dental implant socket) to the optimal angle and depth for a dental implant screw.

Although, as per parent application Ser. No. 13/183,386, the post device may be a linear pole-like device that tends to fix the drilling angle of the guide drill bit at the same angle as the original root socket of the extracted tooth, other post device configurations are also possible. In an alternative embodiment, often it will be useful to use a post device comprising a bottom probe portion that in turn is affixed to a top drilling orientation portion. As per Ser. No. 13/183,386, the bottom probe portion of the post device can comprise an elongated probe with a probe axis. This probe portion will generally have at least one radius small enough to penetrate substantially to the bottom of the empty tooth root socket.

In contrast to Ser. No. 13/183,386, however, the post device can additionally comprise a top drilling orientation portion with a larger radius or diameter portion. The top drilling orientation portion of the post device can have its own drilling axis that is distinct from the probe axis, and this top drilling orientation portion will typically be configured to protrude outside of the tooth root socket. This drilling axis may be (although it need not be) offset from the probe axis, and further this drilling axis need not be at the same angle as the probe axis.

The advantages of separating the position and angle of the top orientation portion of the post device from the position and angle of the bottom probe axis of the post is that, as will be discussed, in many situations, the optimal location for a dental implant socket for a dental implant screw will also be offset by a defined position and angle from the original (i.e. natural) tooth root socket for that particular (former) tooth. Thus although the practitioner may thus wish to drill an implant socket at a somewhat different angle and location relative to the original tooth root socket, still the position and angle of the original tooth root socket, relative to the other structures of the patient's jaw, serves as an excellent reference point for drilling the subsequent implant socket.

In other words, according to the method, the extent to which the drilling axis is offset from the probe axis, and wherein the extent to which the drilling axis is not at the same angle as the probe axis can be determined by the optimal displacement, angle and depth for a dental implant screw relative to the position of the tooth root socket.

To do this, as will be discussed, the practitioner will typically determine the patient's particular tooth and jaw anatomy, and select an appropriate post device with the space offsets and angle offsets appropriate for the situation (i.e. offsets that will give the best results for drilling the dental implant screw later). The practitioner can then place the appropriate post device into the empty tooth root socket, record the position of the post device, as well as the space offsets and angle offsets provided by the top orientation portion of the post device, and later use this to determine the extent to which the drilling axis (for the dental implant socket for the dental implant screw) is not at the same location and angle as the probe axis.

FIG. 1A-1H shows the method in operation on a lower first molar tooth socket, using an offset post device. In this example, the direction of the drilling axis formed by the top drilling orientation portion of the post device is offset, relative to the probe axis (of the bottom probe portion), in a lingual direction so that the drill can drill into the anatomically safe region formed by the jaw bone between the two molar tooth root sockets.

In FIG. 1A, the lower first molar tooth has been extracted, resulting in an empty tooth socket (102). An offset type probe device, here consisting of a bottom probe portion (104) and a top drilling orientation portion (106), and often some smaller "O" rings (114) around the bottom probe portion (104) is lowered into a suitable root socket in the empty tooth socket (102). This is shown in a somewhat magnified view in FIG. 1B. Here the location of the two empty root sockets is shown by dotted lines (112). Note that in this example, the axis of the top drilling orientation portion (106) of the probe device is clearly offset from the axis of the bottom probe portion (104). This type of offset probe device generally corresponds to the lateral placement probe device shown in more detail in FIG. 7A-7F.

As previously discussed in parent application Ser. No. 13/183,386, the contents of which are incorporated herein by reference, such O-rings (114) help center the post in the socket and also help protect the empty tooth socket bony walls (112) from damage due to the bottom probe portion of the post device (104). These O-rings will often be made from somewhat flexible material such as elastic-or semi-elastic material.

After the bottom probe position of the probe device is suitably positioned in the root socket FIG. 1C, a guide sleeve (122) is then lowered into position over the top drilling orientation portion of the probe device. This guide sleeve in position is then shown in FIG. 1C as (132).

The practitioner will then record the position and orientation of the top drilling orientation portion (106), often by constructing a position fixation device or guide device around the guide sleeve (132), as shown in FIG. 1E. This position fixation device (142) stabilizes the position of the guide sleeve (132), and therefore also the top orientation portion of the probe device (106) relative to the position of at least some of the patient's other teeth adjacent to the empty tooth socket (102).

Often this position fixation device or guide (142) may be constructed using a flexible but rapidly hardening material, such as an acrylic or thermoplastic guide material, to construct a position fixation device or guide that contacts at least some of the outer surface of the guide sleeve (132) as well as the outer surface of at least some of the teeth adjacent to tooth socket (102).

Usually the practitioner will work quickly to build up the position fixation device/guide while the guide material is flexible and optionally self-adhesive, and then allow the guide to harden while it is in the patient's mouth. Thus the position fixation device (142), after it has hardened and is rigid, locks the guide sleeve (132) into position relative to the patient's adjacent teeth, and the hole the guide sleeve (132) in turn preserves the position and orientation top drilling orientation portion of the probe device (106) which in turn is determined by the position and orientation of the patient's natural tooth root socket (112).

To generalize, the position fixation device generally comprises a deformable plastic material configured to adhere to the patient's teeth proximate to the extraction socket in the patient's jaw bone. The position fixation device generally grips the guide sleeve (132), so that the guide sleeve itself may become part of the position fixation device as well. This guide sleeve in turn holds both the top drilling orientation portion of the post device, and the deformable plastic material.

Usually when the guide has hardened, but optionally also at other stages in the process, the practitioner may also take standard dental X-rays, or other X-rays as desired, to determine the depth of the post device in the empty tooth socket (112). This can be used later to determine a safe drilling depth for the dental implant. As an example, X-ray film or a solid state X-ray detector can be placed inside the patients mouth near the post, exposed with X-rays from outside the mouth (not shown), and the film or X-ray detector, when analyzed will show the relative depth of the post in the root socket. This information will often be preserved for the subsequent drilling step.

To show up on an X-ray, the post device will often made of a radio opaque material such as aluminum, or plastic doped with a radio opaque material. In some embodiments (in particular see FIG. 5A-5F, FIG. 6A-6F, and FIG. 7A-7F), the post may have a number of X-ray visible markers, such as detents or grooves positioned along the length of the post. Thus the dentist or other practitioner can, after inserting the post, take standard dental X-ray images of the post, and by counting grooves, detents or other X-ray visible markers determine the depth of the natural root socket, and this information in turn can be used later to guide the implant drilling process.

Once the position fixation device (142) is fully formed, it then may be removed from the patient's mouth, along with the probe device. Often the tooth extraction socket will then be filled in (e.g. with bone or other material intended to encourage bone regrowth and healing), and allowed to heal. This healed tooth extraction socket is shown in FIG. 1F as (152).

When drilling a dental implant screw socket is desired, the position fixation device (142) may then be reapplied to the patient's mouth, and usually anchored relative to the teeth adjacent the tooth extraction socket, as shown in FIG. 1G. To reduce the size of the guide sleeve hole down to the appropriate diameter for a drill, a drill reduction guide tool (162) may be placed into the hole in the guide sleeve (132), as is shown in FIG. 1G and FIG. 1H. In some embodiments, it may be useful to use a custom tool that fits a plurality of different diameter drill reduction guide tools onto a single device, as is shown in FIG. 9.

FIG. 2A-2H show the method in operation on an upper canine lateral incisor tooth socket, using an angled post device where the angle of the drilling axis formed by the top drilling orientation portion of the post device is offset, relative to the probe axis (of the bottom probe portion), in a lingual direction to avoid having the drill accidentally drill outside of the jaw bone in the facial direction, as well as to avoid subsequent facial bone resorption.

Dental implants are seldom placed in the center of teeth sockets when the facial bony wall is thin. This is because the facial bony wall usually has inadequate support strength, and, the facial bone usually resorbs after implant placement, exposing the outer surfaces of the implant to the oral environment. Thin facial bone walls are typical of most teeth especially incisors, cuspids and bicuspids. All of these teeth require that the implant to be angled or positioned away from the facial bony wall. Therefore this type post device would be used to offset the angle of the drill guide in the desired orientation.

The method shown in FIG. 2A-2H is generally similar to those previously shown in FIG. 1A-1H, with the exceptions that in FIG. 2A-2H, here the method is optimized to allow the practitioner to drill a dental implant socket for an upper lateral incisor top canine tooth. As a result, due to differences in anatomy between an incisor canine tooth and a molar, with typical patient jaw anatomy, an alternate type of probe device, generally similar to the angled probe device shown in FIG. 6A-6F, is often more appropriate. This is because due to the different anatomy of the jaw in the canine tooth region, it is usually preferable to angle the direction of the drill for the dental implant screw somewhat inward towards the lingual direction (i.e. back of the patient's throat) to avoid inadvertently drilling through the front of the patients jaw. As can be easily imagined, accidentally drilling too close or through the front of the patient's mouth bone and gum at the front of the intended implant will cause much distress, cosmetic damage, and functional damage to the patient, and thus must be carefully avoided.

Figures 2A, 2B, 2C, 2D, 2E, 2F, 2G, 2H:
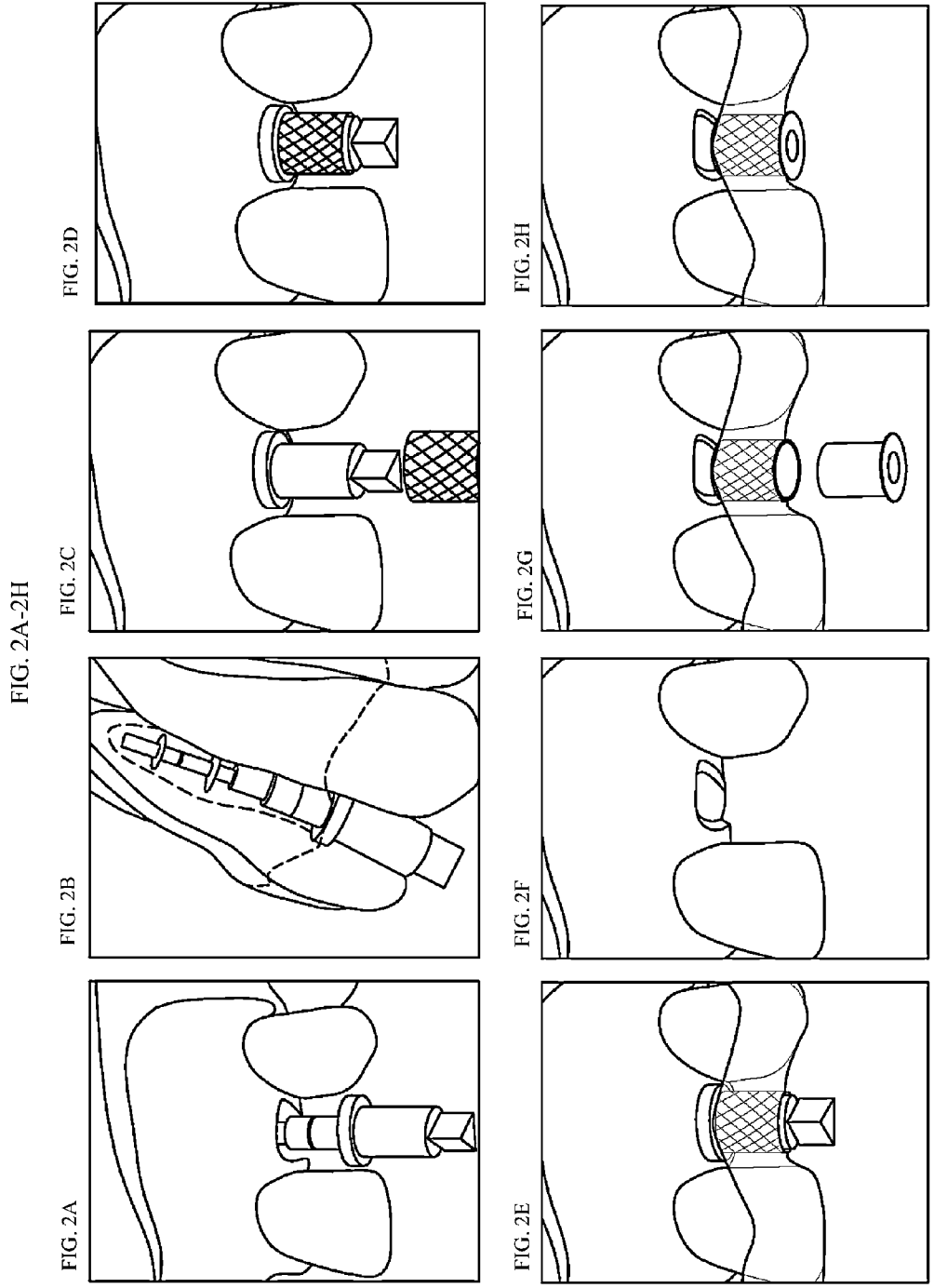
FIG. 2A-2H show the method in operation on an upper lateral incisor tooth socket, using an angled post device where the angle of the drilling axis formed by the top drilling orientation portion of the post device is offset, relative to the probe axis (of the bottom probe portion), in a lingual direction to avoid having the drill accidentally drill outside of the jaw bone in the facial direction, as well as to avoid subsequent facial bone resorption.

Thus in FIG. 2A, a probe device in which the drilling axis of the top drilling orientation portion of the probe device is not at the same angle as the angle of the bottom probe axis of the device is used. As can be seen best in FIG. 2B, when the bottom probe portion of the device is placed in the root socket of this canine incisor tooth, the drilling axis of the top drilling orientation portion of the probe device will (once the location is preserved by the position fixation device) guide the drill for the dental implant screw somewhat away from the front of the patient's mouth, gently angled towards the back lingual portion of the mouth, thus ensuring that the drill will not go through the front of the patient's jaw and mouth. The other steps (FIG. 2C-FIG. 2H) are otherwise similar to those previously shown in FIG. 1A-1H.

Figure 3:
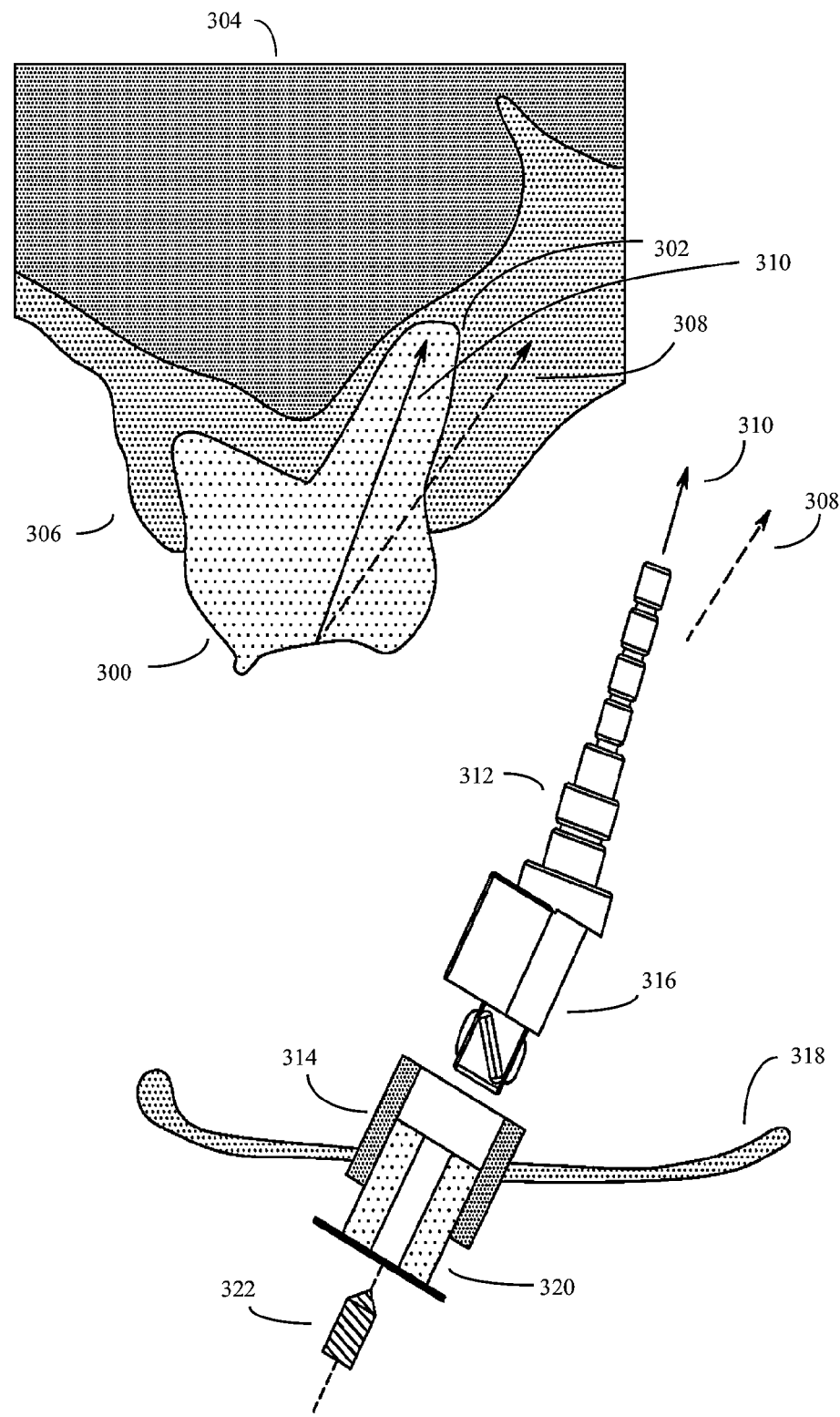
FIG. 3 shows a schematic cross section of an upper molar tooth, illustrating the very narrow distance between the end of the tooth root and the beginning of the patient's open sinus region. Here, in order to safely drill an implant socket, the angle of the top orientation portion of the post device is offset from the angle of the post device's probe axis.

To better understand the difference between the drilling axis controlled by the top drilling orientation portion of the probe device, and the probe axis controlled by the bottom probe portion of the post device, and why this can be so critical for patient safety, consider FIG. 3.

FIG. 3 shows a schematic cross section of an upper molar tooth (300), illustrating the very narrow distance between the end of the tooth root (302) and the beginning of the patient's hollow sinus region (304). Note that accidentally drilling into the sinus region is highly undesirable. The patient's jaw bone is shown in cross section as (306). Here, in order to safely drill an implant socket, the angle of the drilling axis of the top orientation portion of the post device is offset (308) from the angle of the post device's probe axis (310).

Figure 6:
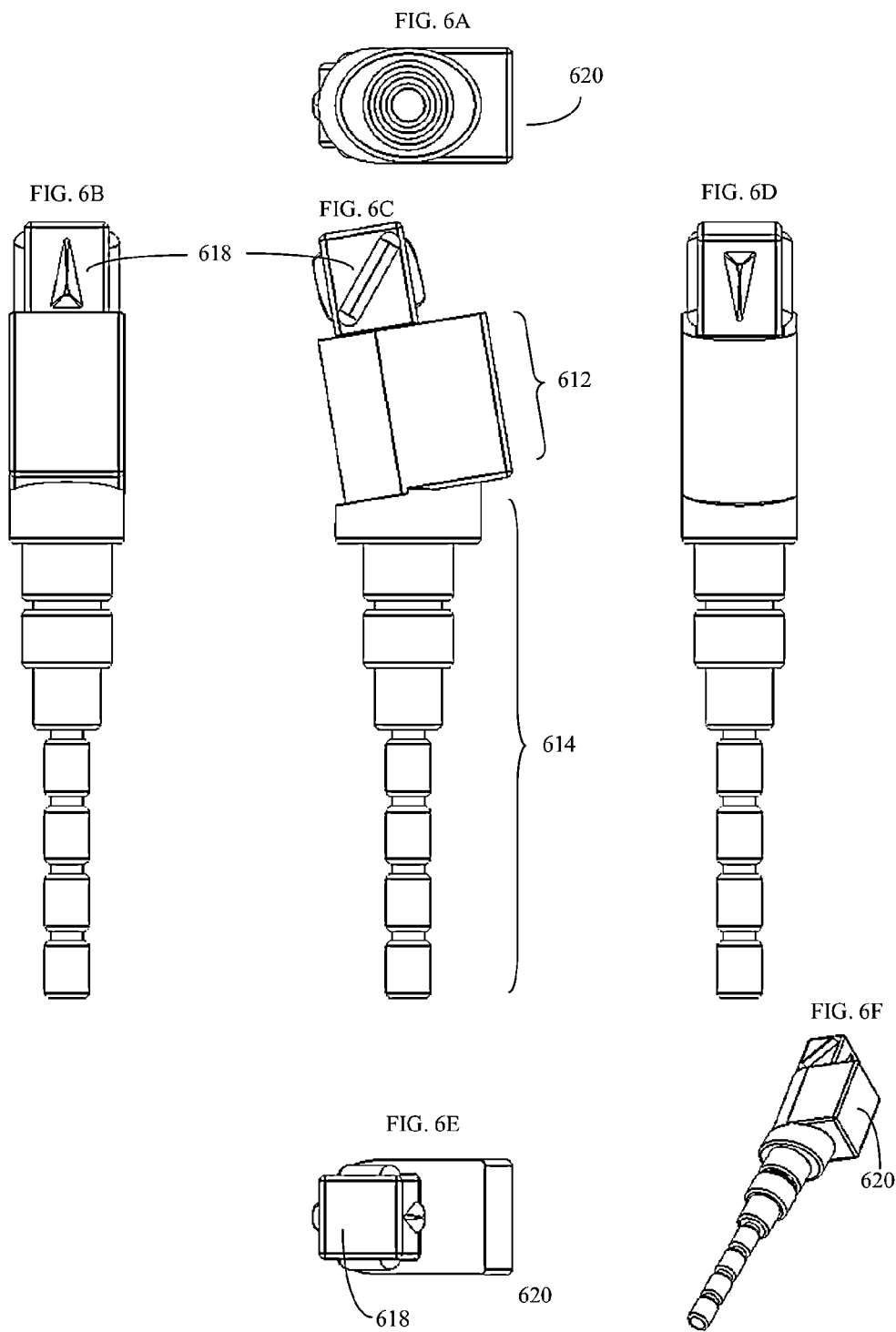
FIG. 6A-6F show a detailed engineering drawing of a second type of post device where the drilling axis of the top orientation portion of the post device forms an angle that is offset from the angle of the device's bottom probe portion probe axis. This post device can also accept an open U-shaped drill guide sleeve which allows drill entry from the open side, as compared to a closed ring drill guide where the drill has to enter from the top.

FIG. 3 (312) shows the approximate position and scale of a suitable probe device, generally designed according to the angled probe device shown in FIG. 6, and the corresponding positions of the probe axis (310) and drilling axis (308). This probe device (312) will fit into the extraction socket and root socket that is formed when tooth (300) is removed. Once in place, a guide sleeve (314) will cover the top drilling orientation portion (316) of probe device (312), and the position and orientation of this guide sleeve will be preserved by the position fixation device (318) (shown in cross section) that will anchor the guide sleeve relative to adjacent teeth (not shown). To drill the dental implant socket for a dental implant screw, the practitioner will often insert a drill reduction guide tool (320) into the center hold in the guide sleeve. The net result is to position the center hole of the guide sleeve and drill reduction tool as to effectively guide a drill bit (322) down the same drilling axis (308) originally determined by probe device (312).

As previously discussed, the angles and locations at which a dental implant socket may be optimally drilled will often systematically vary according to the position and type of tooth in the mouth. Although there will be individual variations within this overall pattern, the general trend is consistent enough that a useful kit of different probe devices, optimized for different teeth, may be produced. This kit of probe devices may additionally be supplemented by other probe devices as well, which may be optimized to cope with abnormal tooth and jaw situations. The kit may also contain various washers, guide sleeves, open guide sleeves (for side drilling, to be discussed), position location device materials, and other materials.

Figure 4:
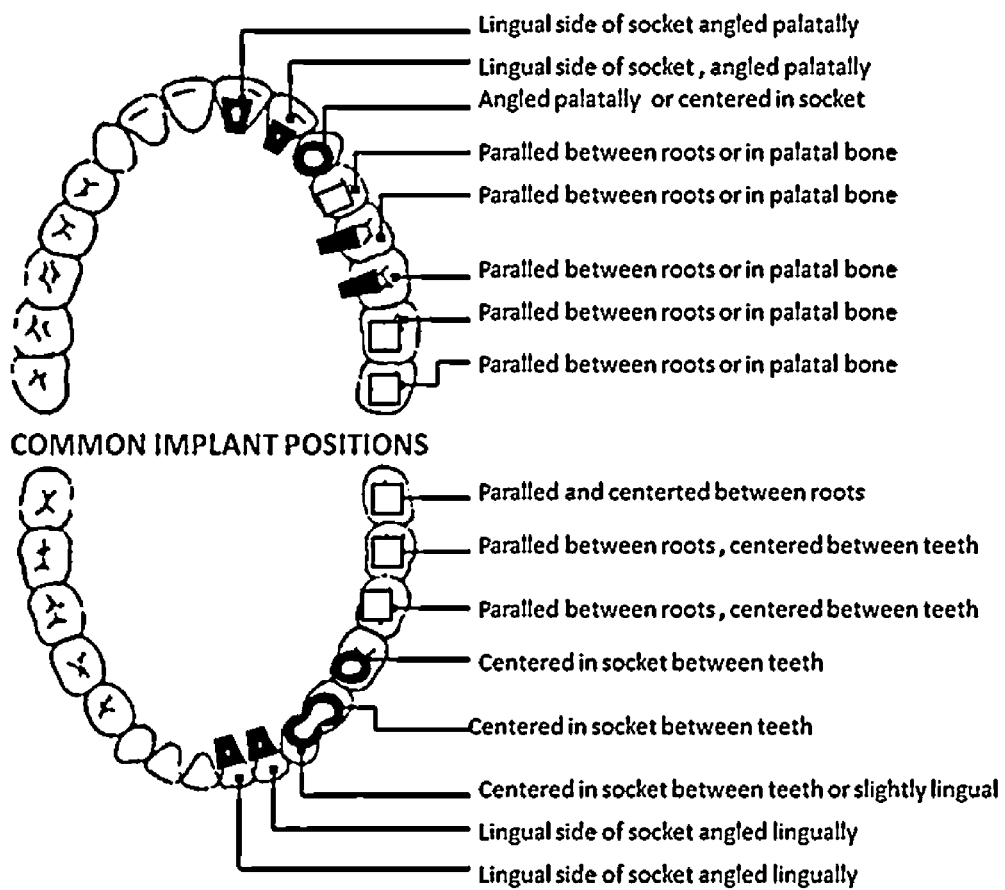
FIG. 4 shows a schematic drawing of the teeth in a normal adult human jaw, showing the typical offset considerations between the drilling axis of the top orientation portion of the post device, and the angle of the post device's probe axis (of the bottom probe portion), needed for various post devices optimized for drilling implant sockets for the various typical tooth positions. Such considerations can be used to provide kits consisting of a plurality of various different post devices, with structures optimized for various tooth positions.
Figure 5:
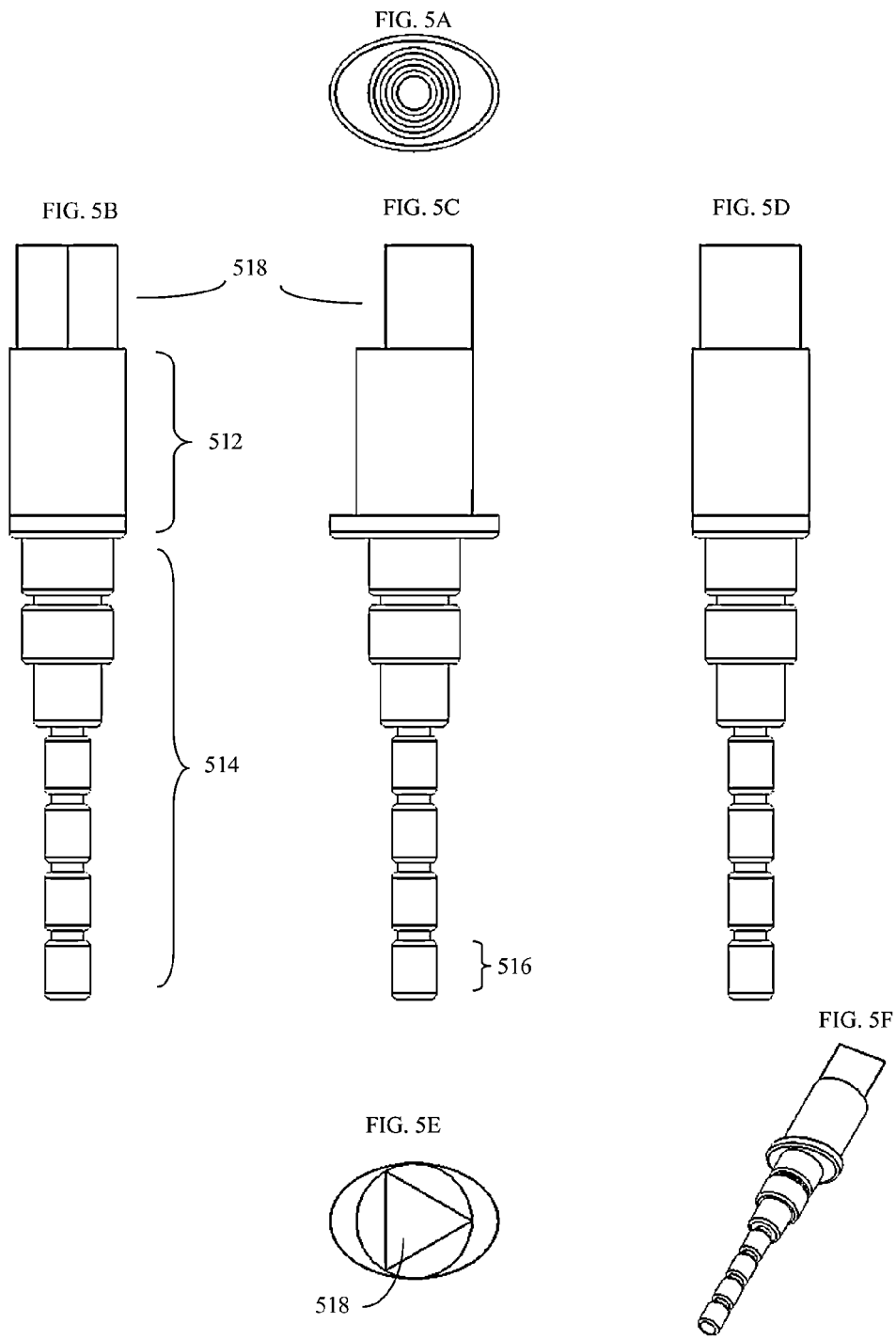
FIG. 5A-5F show a detailed engineering drawing of a first type of post device where the drilling axis of the top orientation portion of the post device is not offset in either angle or direction from the device's bottom probe portion probe axis.

FIG. 4 shows a schematic drawing of the teeth in a normal adult human jaw, showing the typical offsets between the drilling axis of the top orientation portion of the post device and the angle of the post device's probe axis (of the bottom probe portion) needed for various post devices optimized for various typical tooth positions. Such considerations can be used to provide kits consisting of a plurality of various different post devices, with structures optimized for various tooth positions.

Thus generally, the post device used for a particular tooth implant may be selected from a kit of various different standard post devices configured for at least some of the various positions that different human teeth occupy in human jaws. For many of the post devices in this kit, the extent to which the post device's drilling axis is offset from the post device's probe axis and the extent to which the post device drilling axis is not at the same angle as the post device's probe axis, may often be pre-determined based on either considerations of typical human jaw and tooth anatomy, considerations of atypical human jaw and tooth anatomy, or considerations of that particular patient's individual jaw and tooth anatomy.

FIG. 5A-5F show a detailed engineering drawing of a first type of post device where the drilling axis of the top orientation portion of the post device is not offset in either angle or direction from the device's bottom probe portion probe axis. This drawing shows the device from the bottom FIG. 5A, three various sides FIG. 5B, FIG. 5C, FIG. 5D, the top FIG. 5E and in perspective FIG. 5F. The top drilling orientation portion is shown as (512), and the bottom probe portion is shown as (514). The bottom probe portion may have optional indentations or indicia every few millimeters (516), such as every three millimeters, to help determine the distance to the bottom of the tooth root socket.

In some embodiments, the top orientation portion of the device may additionally have various indicia and features (518) to help the dentist determine the orientation of the probe portion and probe axis relative to the orientation of the top drilling orientation portion and the drilling axis. The indicia or features can also help remind the dentist what type of probe device is in use. Here a triangular indicia or feature is shown (518).

In this particular example, the drilling axis is at the same orientation and angle as the probe axis.

By contrast, FIG. 6A-6F shows a detailed engineering drawing of a second type of post device where the drilling axis of the top orientation portion of the post device forms an angle that is offset from the angle of the device's bottom probe portion probe axis. This type of device, although not identical in all aspects, was previously shown in FIG. 2A-2H.

This drawing shows the device from the bottom FIG. 6A, three various sides FIG. 6B, FIG. 6C, FIG. 6D, the top FIG. 6E and in perspective FIG. 6F. The top drilling orientation portion is shown as (612), and the bottom probe portion is shown as (614). Note that the top drilling orientation portion has a different angle from the bottom probe portion, and thus the drilling axis of this portion is different from the probe axis of the bottom probe portion (614). As before, the bottom probe portion may have optional indentations or indicia every few millimeters, such as every three millimeters, to help determine the distance to the bottom of the tooth root socket.

In some embodiments, the top orientation portion of the device may additionally have various indicia and features (618) to help the dentist determine the orientation of the probe portion and probe axis relative to the orientation of the top drilling orientation portion and the drilling axis. The indicia or features can also help remind the dentist what type of probe device is in use. Here a square indicia with various markings or features is shown (618).

Because, in this particular example, the drilling axis is at a different orientation and angle from the probe axis, it is important for the dentist to clearly see which way the angle goes. This is done by the protruding square feature (620), positioned opposite the angle bend. This feature (620) also helps prevent the post device from rotating when the position fixation device is used to preserve the position and orientation of the post device relative to the patient's teeth and jaw bone. When an asymmetric top drilling orientation portion (612) such as this is used, often the guide sleeve will also have a similarly asymmetric hole to fit closely over the asymmetric top drilling orientation portion.

Put alternatively, when the post device is in the socket and the metal sleeve is attached to the position fixation device, all that is visible is the protruding square feature with the orientation markings. These markings indicate the exact spatial positioning of the post and guide relative to the jawbone. The dentist does not have to remove the entire assembly from the socket to confirm that the angulation of the post probe is correct.

FIG. 7A-7F show a detailed engineering drawing of a third type of post device where the drilling axis of the top orientation of the post device is offset (i.e., not collinear with) by some distance from the device's bottom probe portion probe axis. This type of offset device (although not identical in all aspects) was previously shown in FIG. 1A-1H.

Figure 7:
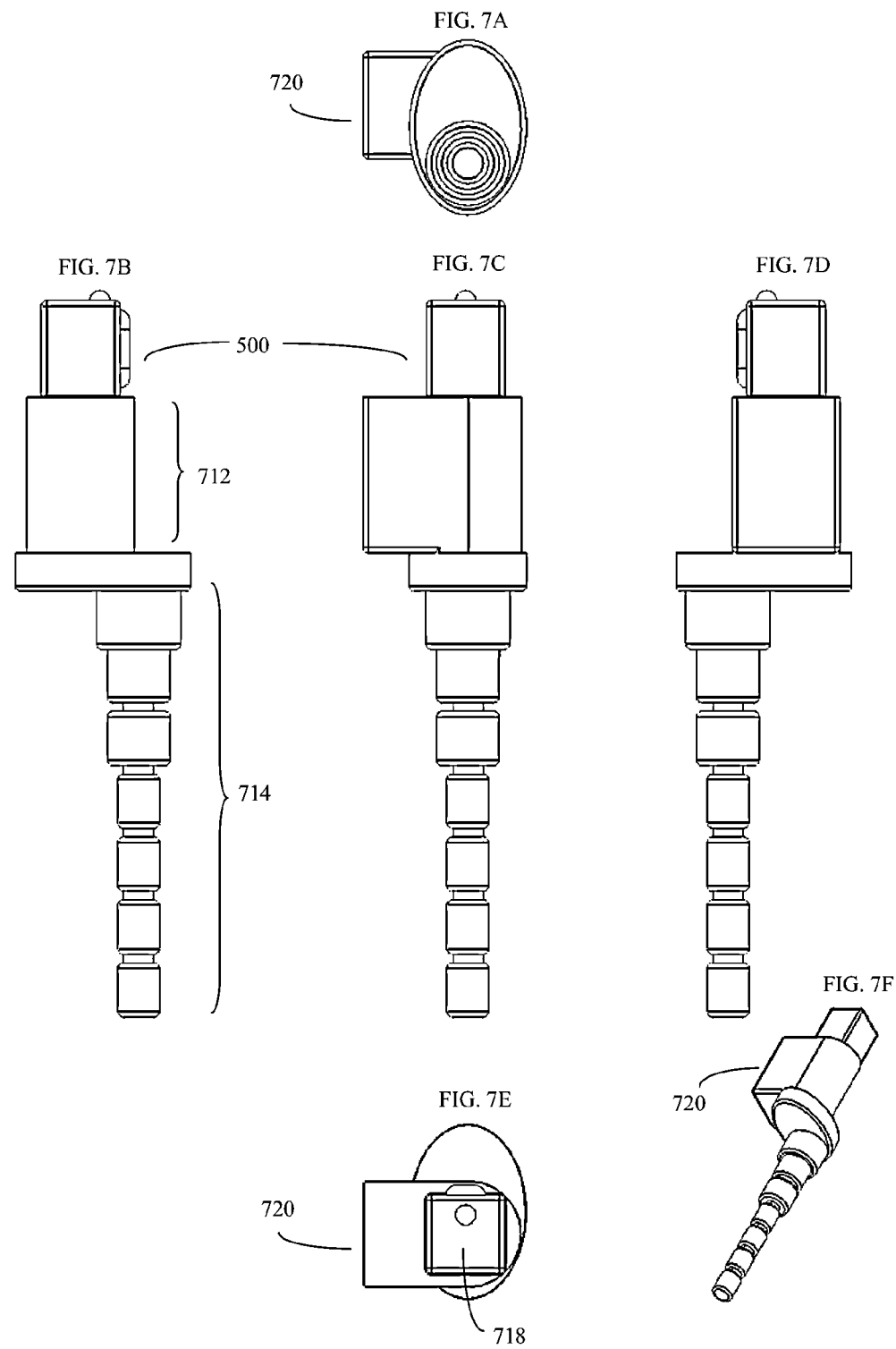
FIG. 7A-7F show a detailed engineering drawing of a third type of post device where the drilling axis of the top orientation portion of the post device is offset (i.e., not collinear with) by some distance from the device's bottom probe portion probe axis.

This drawing again shows the device from the bottom FIG. 7A, three various sides FIG. 7B, FIG. 7C, FIG. 7D, the top FIG. 7E and in perspective FIG. 7F. The top drilling orientation portion is shown as (712), and the bottom probe portion is shown as (714). Note that the top drilling orientation portion is displaced from the bottom probe portion, and thus the drilling axis of this portion is displaced from the probe axis of the bottom probe portion (714). As before, the bottom probe portion may have optional indentations or indicia every few millimeters, such as every three millimeters, to help determine the distance to the bottom of the tooth root socket.

In some embodiments, the top orientation portion of the device may additionally have various indicia and features (718) to help the dentist determine the orientation of the probe portion and probe axis relative to the orientation of the top drilling orientation portion and the drilling axis. The indicia or features can also help remind the dentist what type of probe device is in use. Here a square indicia with various markings or features different from those shown previously is shown (718).

Because, in this particular example, the drilling axis is offset from the probe axis, it is again important for the dentist to clearly see which way the offset goes. This is again done by the protruding square feature (720), here positioned in the same direction as the offset. This feature (720) also helps prevent the post device from rotating when the position fixation device is used to preserve the position and orientation of the post device relative to the patient's teeth and jaw bone. When an asymmetric top drilling orientation portion (712) such as this is used, often the guide sleeve will also have a similarly asymmetric hole to fit closely over the asymmetric top drilling orientation portion.

Figure 8:
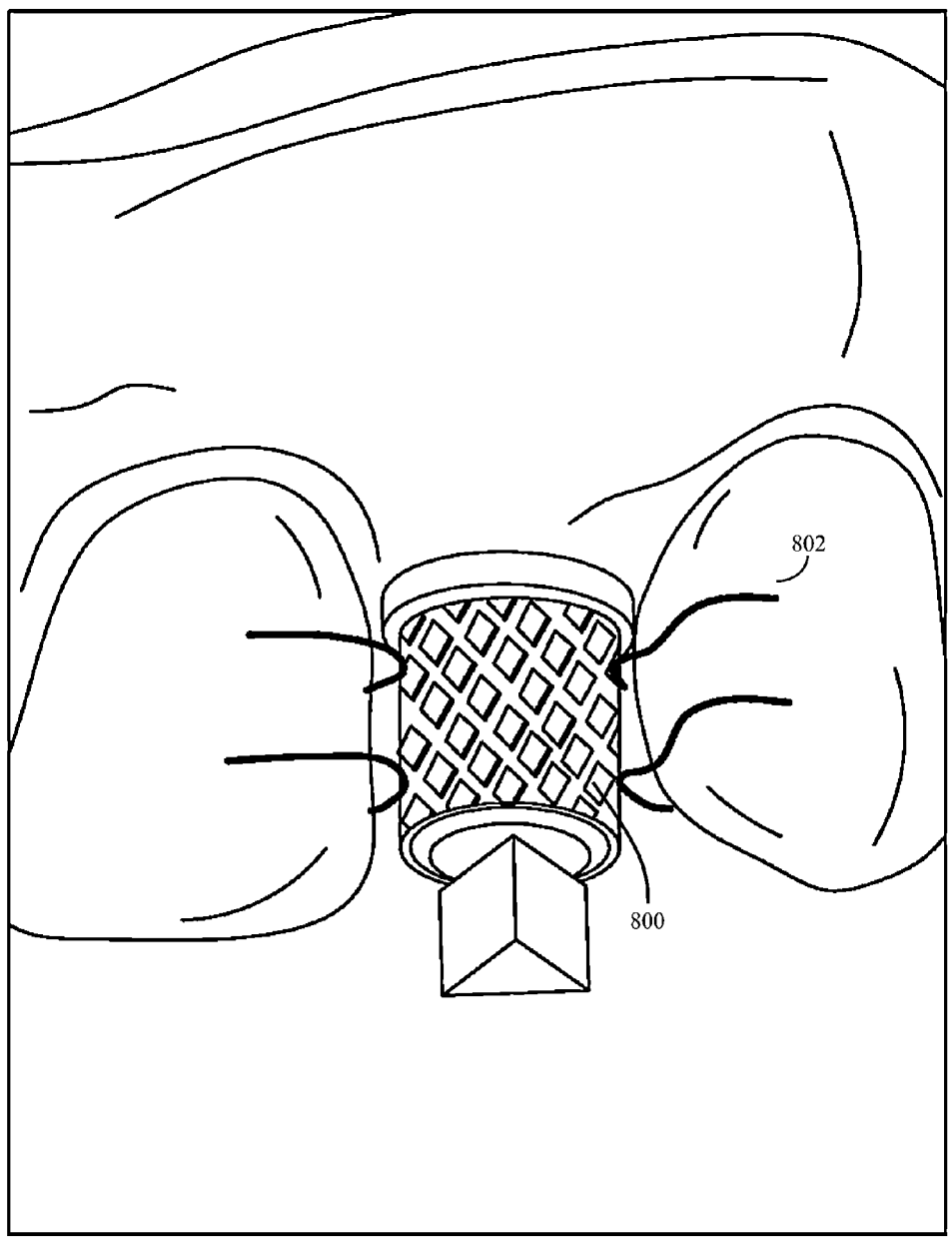
FIG. 8 shows an example where a circular O-shaped guide sleeve, which can be used as part of the position fixation device to preserve the position and orientation of the post device relative to the jaw bone, additionally comprises some surface appendages or attachments to help further stabilize the position and orientation of the sleeve and post device relative to adjacent teeth.

FIG. 8 shows an example of an alternate guide sleeve (800) configuration. As before, this guide sleeve may later also be used as part of the position fixation device to preserve the position and orientation of the post device relative to the patient's jaw and teeth. Here, this alternate device additionally comprises various surface appendages or attachments (802), such as bendable plastic or metal wires or other protruding fixtures, to help further stabilize the position and orientation of the guide sleeve and the inside post device relative to the patient's adjacent teeth. These attachments can also block out undercut surfaces on the adjacent teeth so that the position fixation device can be easily removed after fabrication.

Note that many different types of guide sleeves are possible. This is because the guide sleeve will have a hollow interior to fairly precisely match the top drilling orientation portion of the guide sleeve's corresponding post device. Guide sleeves can be made of a variety of materials, such as stainless steel, plastic, or other materials. In some embodiments (not shown) one side of the guide sleeve may be open, thus allowing the dentist to apply an angled drill from the side of the guide sleeve, rather than from the top. This side opening type guide sleeve is particularly useful for working in tight spaces in the mouth, where there may not be enough room to work to apply the drill from the top of the guide sleeve opening.

Since all of these procedures have to be done in the very small amount of space inside the patient mouth, often other oral structures in the patient's mouth, such as the patient's tongue, lips, and cheeks, have to be moved out of the way during the drilling process. To do this, it is often useful to mount the drill reduction guides onto a tool that both holds the drill reduction guide or guides, and also helps the dentist push the other mouth oral structures out of the way during the procedure. An example of such a tool is shown in FIG. 9A and FIG. 9B.

Figure 9A:
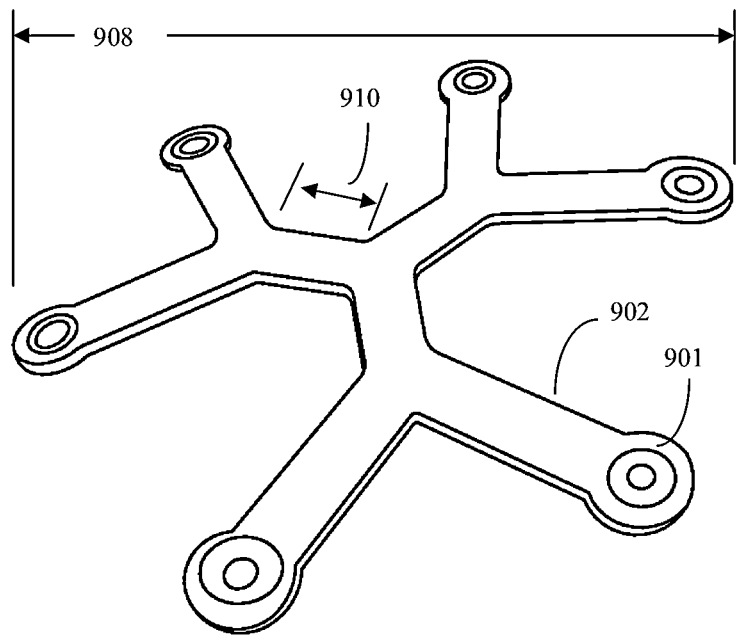
FIG. 9A-9B show an example of a drill reduction guide tool, useful for the method, that both centers multiple drill sizes in various guide sleeves for implant socket drilling, while also at the same time has a unique branched wheel type design with multiple arms where some of the arms can also be also used to help reposition the soft tissues of the patient's mouth (i.e. inner cheeks, tongue, and the like) during the procedure.
Figure 9B:
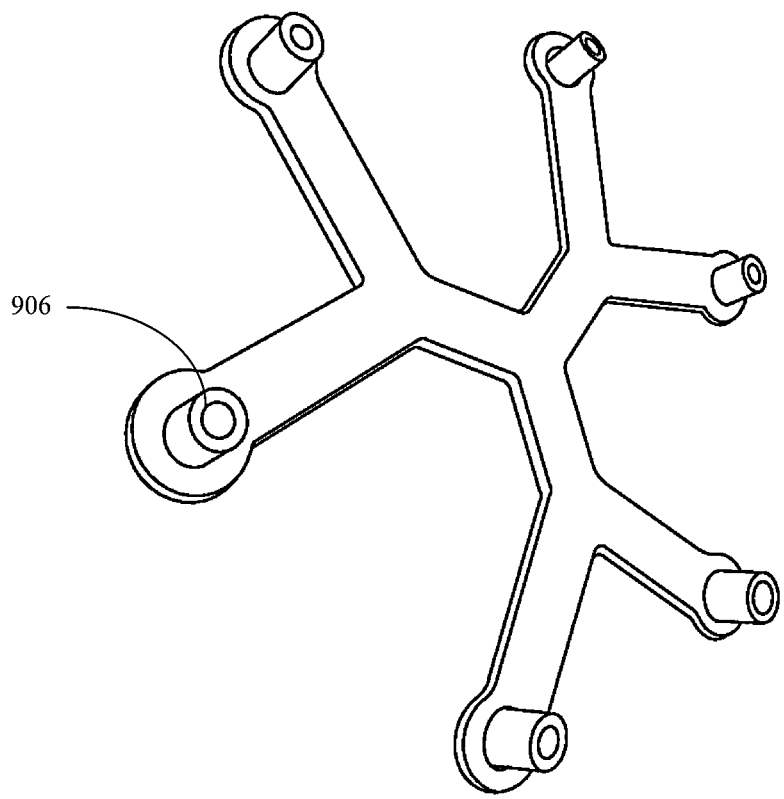

FIG. 9A-9B show an example of a drill reduction guide tool, useful for the invention's method, that both centers multiple drill sizes in various guide sleeves for implant socket drilling, and also at the same time has a unique branched-wheel type design with multiple arms where some of the arms can also be also used to help reposition the soft tissues of the patient's mouth during the procedure.

On the top FIG. 9A, the diameter of the various drill bit openings (901) is shown in millimeters (902). On the bottom FIG. 9B, the protruding drill guides, which fit inside the guide sleeves, are also shown (906). In this example, the drill guide has an overall diameter of about 90 millimeters (908), and the distance between the various "Y" branching is about 16.5 millimeters (910). Other dimensions and configurations may also be used.

In some cases, the dental implant screws may be used to support bridges spanning multiple teeth. In this sort of situation, often two dental implant screws are used, and it is important that the sockets for the two dental implant screws be precisely parallel. To assist in this process, it may additionally be useful to use another type of guide to insure that parallel holes are drilled, such as the "wishbone" shape guide shown in FIG. 10.

Figure 10:
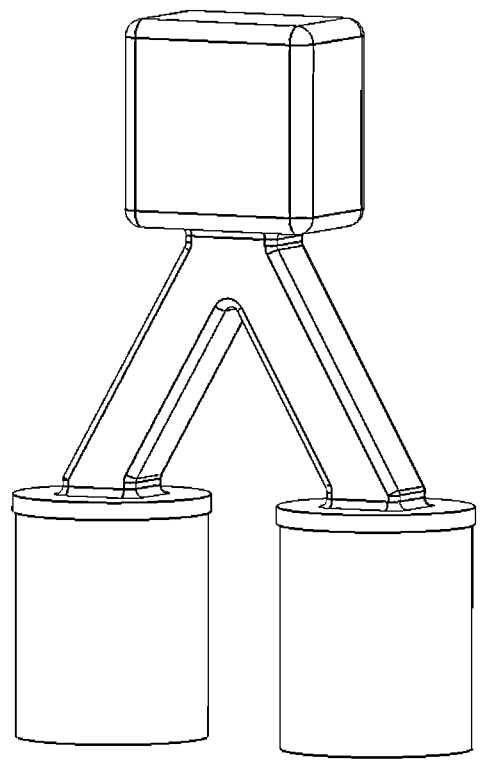
FIG. 10 shows an example of a parallel wishbone guide that facilitates drilling of adjacent parallel implant sockets for bridge type implants spanning more than one tooth. In some embodiments, the wishbone guide may be used to drill a parallel implant socket in the next tooth, while in other embodiments; the wishbone guide may have a wider separation to enable parallel implant bridges to skip over a missing tooth.

FIG. 10 shows an example of a parallel wishbone guide that facilitates drilling of adjacent parallel implant sockets. In some embodiments, the wishbone guide may be used to drill a parallel implant socket in the next tooth, while in other embodiments; the wishbone guide may have a wider separation to enable parallel implant bridges to skip over a missing tooth.

The invention claimed is:

1. A method of drilling a dental implant socket for a dental implant screw in the mouth of a patient after extracting a tooth from the jaw bone of said patient, thereby forming an extraction socket in said jaw bone with at least one tooth root socket in said jaw bone corresponding to the position of at least one root of said tooth, said method comprising:
    while said extraction socket remains open and unhealed, placing a post device into said at least one tooth root socket;
    wherein said post device is configured to determine the depth and angle of said tooth root socket relative to said jaw bone;
    said post device additionally configured to also serve as a template for guiding a drill bit for drilling said dental implant socket at an optimal angle and depth for a dental implant screw;
    wherein said optimal angle and depth for said dental implant screw need not be the same angle and depth of said tooth root socket;
    using a position fixation device to preserve the position and orientation of said post device relative to said jaw bone;
    removing said post device from said patient's mouth; and
    using said position fixation device to subsequently guide said drill bit to the optimal angle and depth for a dental implant screw.

2. The method of claim 1, wherein after said post device is removed from said patient's mouth, filling said tooth root socket with material intended to promote the formation of new bone in said tooth root socket, and allowing said extraction socket to heal.

3. The method of claim 1, wherein said post device comprises a bottom probe portion and a top drilling orientation portion;
    said bottom probe portion comprising an elongated probe with a probe axis, said probe having at least one radius small enough to penetrate substantially to the bottom of said tooth root socket;
    said top drilling orientation portion comprising a larger radius or diameter portion with a drilling axis, said top drilling orientation portion configured to protrude outside of said tooth root socket;
    wherein said drilling axis need not be on said probe axis, and wherein said drilling axis need not be at the same angle as said probe axis.

4. The method of claim 3, wherein the extent to which the drilling axis is offset from said probe axis and wherein the extent to which said drilling axis is not at the same angle as said probe axis is determined by the optimal displacement, angle and depth for a dental implant screw relative to the position of said tooth root socket.

5. The method of claim 3, wherein said post device is selected from a plurality of standard post devices configured for at least some of the various positions that different human teeth occupy in human jaws, wherein for said individual post device in said plurality of post devices, the extent to which the drilling axis is offset from with said probe axis and the extent to which said drilling axis is not at the same angle as said probe axis, is pre-determined based on either considerations of typical human jaw and tooth anatomy, considerations of atypical human jaw and tooth anatomy, or considerations of said patient's individual jaw and tooth anatomy.

6. The method of claim 3, wherein the angle at which said drilling axis is not at the same angle as said probe axis is visibly marked on said drilling orientation portion so that indicia of the differences between the drilling axis angle and the probe axis angle are visible to a human dentist.

7. The method of claim 3, wherein said top drilling orientation portion further comprises one or more features that prevent said post device from rotating when said position fixation device is used to preserve the position and orientation of said post device relative to said jaw bone.

8. The method of claim 3, wherein said position fixation device comprises a deformable plastic material configured to adhere to the patient's teeth proximate said extraction socket in the jaw bone of said patient, and at least one sleeve configured to hold both said top drilling orientation portion of said post device, and said deformable plastic material.

9. The method of claim 3, wherein said bottom probe portion comprises a plurality of distance indicia so that the depth of said bottom probe in said tooth root socket is thereby determined.

10. The method of claim 1, wherein said post device is made from a radio-opaque material, or a non-radio opaque material doped with a radio opaque material, such that said post device is visible in a standard dental X-ray.

* * * * *